(12) United States Patent
Gessner et al.

(10) Patent No.: US 10,059,797 B2
(45) Date of Patent: Aug. 28, 2018

(54) PREPARATION OF POLYMERS COMPRISING AT LEAST ONE BENZO[C][1,2,5]THIADIAZOL-5,6-DICARBONITRILE-UNIT

(71) Applicants: BASF SE, Ludwigshafen (DE); Max-Planck-Gesellschaft zur Foerderung der Wissenschaften e.V., Munich (DE)

(72) Inventors: Thomas Gessner, Heidelberg (DE); Helmut Reichelt, Neustadt (DE); Jakob Jacek Wudarczyk, Mainz (DE); Felix Peter Hinkel, Wiesbaden (DE); Tomasz Marszalek, Mainz (DE); Martin Baumgarten, Mainz (DE); Klaus Muellen, Cologne (DE)

(73) Assignees: BASF SE, Ludwigshafen (DE); Max-Planck-Gesellschaft zur Foerderung der Wissenschaften e.V., Munich (DE)

(*) Notice: Subject to any disclaimer, the term of this patent is extended or adjusted under 35 U.S.C. 154(b) by 0 days.

(21) Appl. No.: 15/528,897

(22) PCT Filed: Nov. 23, 2015

(86) PCT No.: PCT/EP2015/077364
§ 371 (c)(1),
(2) Date: May 23, 2017

(87) PCT Pub. No.: WO2016/083303
PCT Pub. Date: Jun. 2, 2016

(65) Prior Publication Data
US 2017/0327634 A1 Nov. 16, 2017

(30) Foreign Application Priority Data

Nov. 24, 2014 (EP) .................................. 14194430

(51) Int. Cl.
| *C08G 75/00* | (2006.01) |
|---|---|
| *C08G 61/12* | (2006.01) |
| *C07D 285/14* | (2006.01) |
| *H01L 51/00* | (2006.01) |
| *H01L 51/05* | (2006.01) |
| *H01L 51/10* | (2006.01) |

(52) U.S. Cl.
CPC ......... *C08G 61/126* (2013.01); *C07D 285/14* (2013.01); *H01L 51/0036* (2013.01); *H01L 51/0043* (2013.01); *C08G 2261/143* (2013.01); *C08G 2261/1412* (2013.01); *C08G 2261/3223* (2013.01); *C08G 2261/3246* (2013.01); *C08G 2261/92* (2013.01); *H01L 51/0003* (2013.01); *H01L 51/0021* (2013.01); *H01L 51/0545* (2013.01); *H01L 51/0558* (2013.01); *H01L 51/105* (2013.01)

(58) Field of Classification Search
CPC . C08G 75/32; C08G 2261/91; H01L 51/0047; Y02E 10/549
See application file for complete search history.

(56) References Cited

U.S. PATENT DOCUMENTS

| 2013/0247989 A1 | 9/2013 | Bazan et al. |
| 2015/0218115 A1* | 8/2015 | Marder ................ C07D 285/14 544/353 |

OTHER PUBLICATIONS

International Search Report dated Jan. 14, 2016 in PCT/EP2015/077364 filed Nov. 23, 2015.
(Continued)

Primary Examiner — Shane Fang
(74) Attorney, Agent, or Firm — Oblon, McClelland, Maier & Neustadt, L.L.P.

(57) ABSTRACT

A polymer containing at least one unit of formula

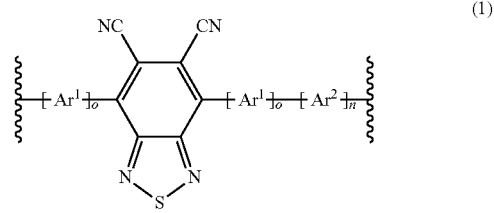

(1)

is prepared by treating a compound of formula

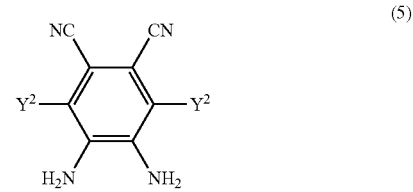

(5)

wherein $Y^2$ is I, Br, Cl or $O-S(O)_2CF_3$,
with an S-donor agent, in order to obtain the compound of formula

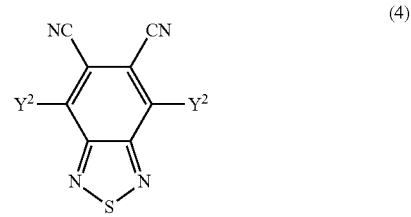

(4)

wherein $Y^2$ is as defined for the compound of formula (5).

9 Claims, 1 Drawing Sheet

(56) References Cited

OTHER PUBLICATIONS

Casey, et al., "Cyano substituted benzothiadiazole: a novel acceptor inducing n-type behavior in conjugated polymers", Journal of Materials Chemistry C, vol. 3, No. 2, XP055167469, Jan. 14, 2015, 12 Pages.

Medlej, et al., "Fluorinated benzothiadiazole-based low band gap copolymers to enhance open-circuit voltage and efficiency of polymer solar cells", European Polymer Journal, vol. 59, XP055167491, 2014, pp. 25-35.

Wang, et al., "Fluorinated Benzothiadiazole-Based Conjugated Polymers for High-Performance Polymer Solar Cells without Any Processing Additives or Post-treatments", Journal of the American Chemical Society, vol. 135, No. 45, XP055167494, 2013, pp. 17060-17068.

International Search Report and Written Opinion dated Jan. 14, 2016 in PCT/EP2015/077364.

International Preliminary Report on Patentability and Written Opinion dated Jun. 8, 2017 in PCT/EP2015/077364.

Extended European Search Report dated Feb. 19, 2015 in Patent Application No. 14194430.6.

* cited by examiner

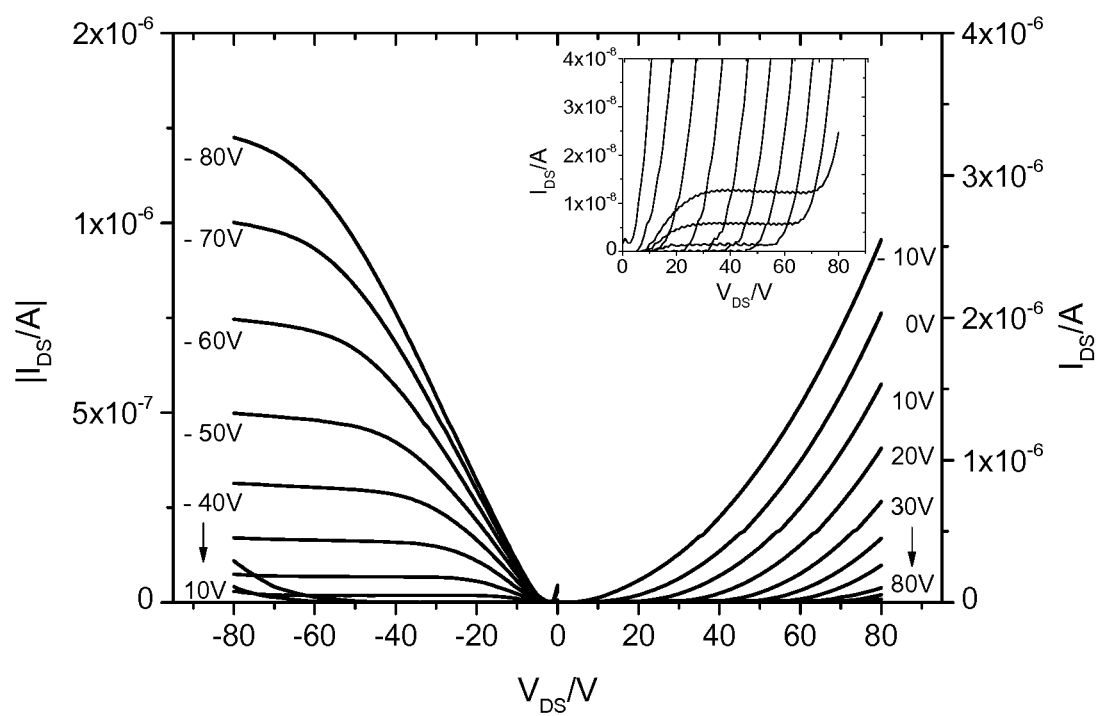

PREPARATION OF POLYMERS COMPRISING AT LEAST ONE BENZO[C][1,2,5]THIADIAZOL-5,6-DICARBONITRILE-UNIT

Organic semiconducting materials can be used in electronic devices such as organic photovoltaic devices (OPVs), organic field-effect transistors (OFETs), organic light emitting diodes (OLEDs), and organic electrochromic devices (ECDs).

For efficient and long lasting performance, it is desirable that the organic semiconducting material-based devices show high charge carrier mobility as well as high stability.

Furthermore, it is desirable that the organic semiconducting materials are compatible with liquid processing techniques such as spin coating as liquid processing techniques are convenient from the point of processability, and thus allow the production of low cost organic semiconducting material-based electronic devices. In addition, liquid processing techniques are also compatible with plastic substrates, and thus allow the production of light weight and mechanically flexible organic semiconducting material-based electronic devices.

The organic semiconducting materials can be a p-type, an n-type or an ambipolar (showing p-type and n-type behavior) organic semiconducting materials.

Casey, A.; Han, Y.; Fei, Z.; White A. J. P.; Anthopoulos, T. D.; Heeney, M. J. Mat. Chem C, 2014, DOI: 10.1039/C4tc02008a describes polymers comprising at least one benzo[c][1,2,5]thiadiazole-5,6-dicarbonitrile-unit and their use as semiconducting material in electronic devices.

The process for the preparation of the polymers comprising at least one benzo[c][1,2,5]thiadiazole-5,6-dicarbonitrile-unit of Casey et al. start form It was the object of the present invention to provide an improved process for the preparation of polymers comprising at least one benzo[c][1,2,5]thiadiazole-5,6-dicarbonitrile-unit.

This object is solved by the processes of claims 1 and 8, the compound of claim 9.

The process of the present invention is a process for the preparation of the polymers comprising at least one unit of formula (1)

wherein $Ar^1$ and $Ar^2$ are independently from each other and at each occurrence $C_{6-14}$-arylene or a 5 to 15 membered heteroarylene, wherein $Ar^1$ and $Ar^2$ can be substituted with one to four substituents selected from the group consisting of $C_{1-30}$-alkyl, CN and $C_{6-14}$-aryl, and wherein at least two adjacent $Ar^1$, respectively, at least two adjacent $Ar^2$ can be additionally connected via an $-(L)_m-$ linker, wherein L is at each occurrence selected from the group consisting of $CR^1R^2$, $C=CR^1R^2$, $C=O$ and $SiR^1R^2$, wherein $R^1$ and $R^2$ are individually from each other and at each occurrence H or $C_{1-20}$-alkyl, and m is 1 or 2, o is an integer from 1 to 8, and n is an integer from 1 to 8, which process comprises the step of (i) treating a compound of formula (5)

wherein $Y^2$ is I, Br, Cl or $O-S(O)_2OF_3$.

with an S-donor agent, in order to obtain the compound of formula (4)

wherein $Y^2$ is as defined for the compound of formula (5).

The S-donor-agent is preferably thionyl chloride. The reaction is usually performed at elevated temperatures, such as at temperatures in the range of 30 to 100° C., preferably at temperatures in the range of 40 to 70° C.

$C_{1-6}$-alkyl, $C_{1-20}$-alkyl and $C_{1-30}$-alkyl can be branched or unbranched. Examples of $C_{1-6}$-alkyl are methyl, ethyl, n-propyl, isopropyl, n-butyl, sec-butyl, isobutyl, tert-butyl, n-pentyl, neopentyl, isopentyl, n-(1-ethyl)propyl and n-hexyl. Examples of $C_{1-20}$-alkyl are $C_{1-6}$-alkyl and n-heptyl, n-octyl, n-(2-ethyl)hexyl, n-nonyl, n-decyl, n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$). Examples of $C_{1-30}$-alkyl, $C_{1-36}$-alkyl, $C_{1-50}$-alkyl, $C_{1-60}$-alkyl and $C_{1-100}$-alkyl are $C_{1-20}$-alkyl and n-docosyl ($C_{22}$), n-tetracosyl ($C_{24}$), n-hexacosyl ($C_{26}$), n-octacosyl ($C_{28}$) and n-triacontyl ($C_{30}$).

Examples of C$_{6-10}$-arylene are
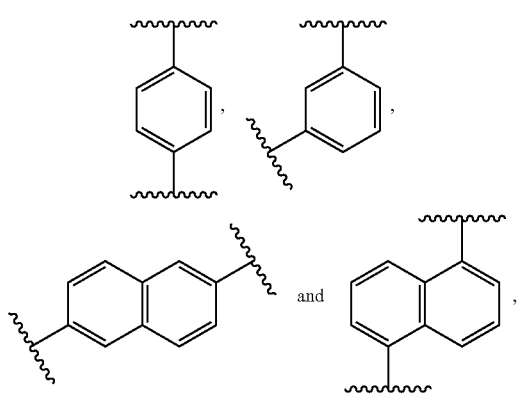
Examples of C$_{6-14}$-arylene are C$_{6-10}$-arylene and
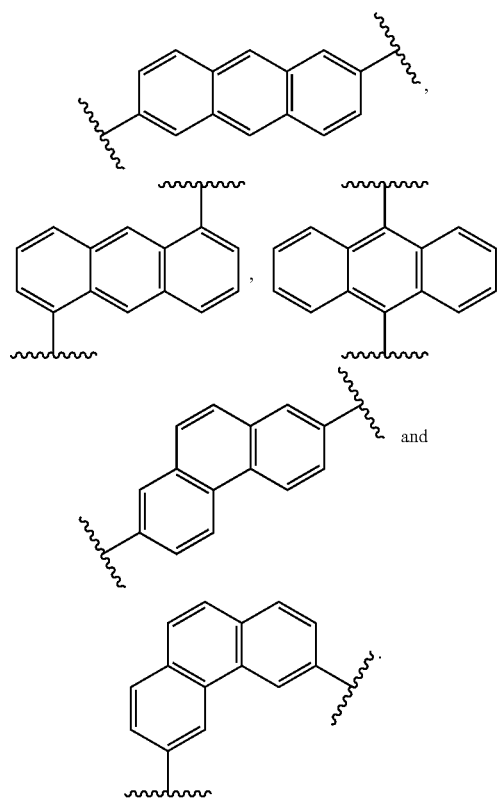
Examples of 5 membered heteroarylene are
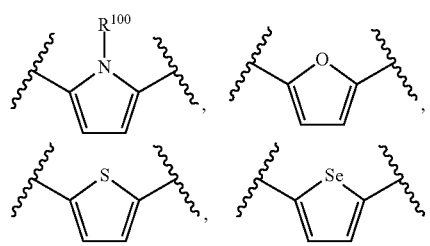
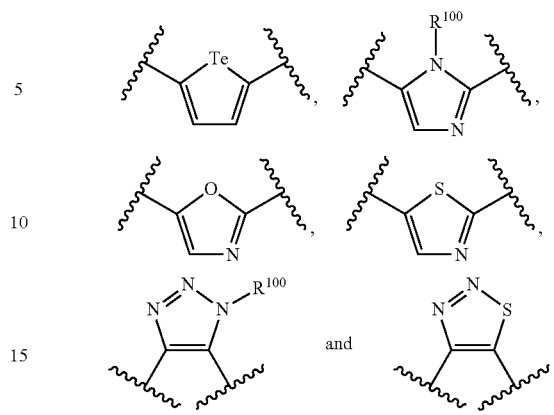
wherein R$^{100}$ is C$_{1-20}$-alkyl.
Examples of 5 to 9 membered heteroarylene are 5-membered heteroarylene and
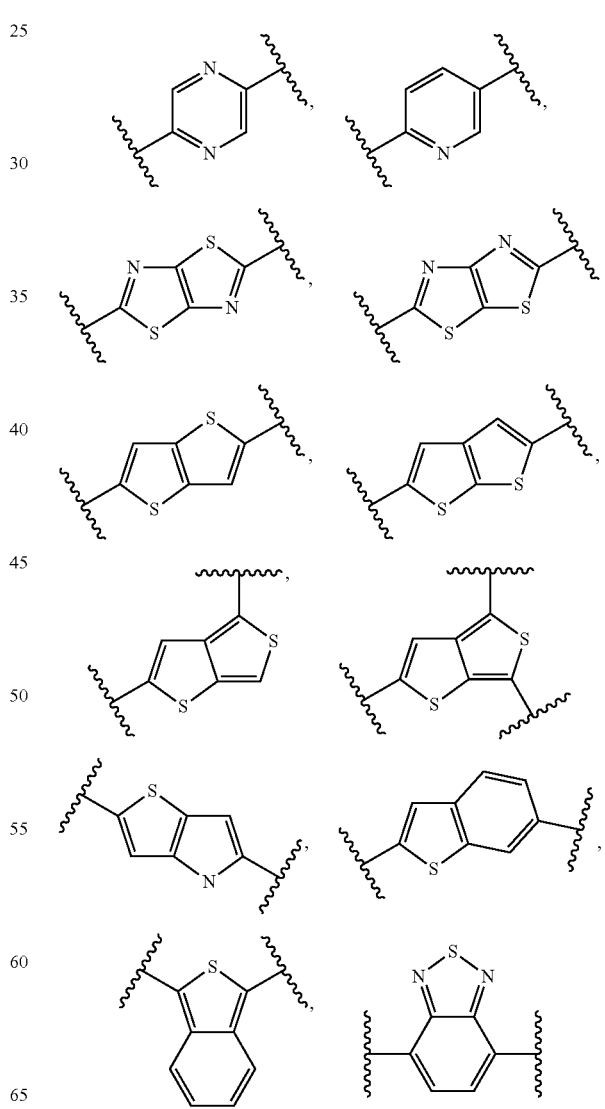

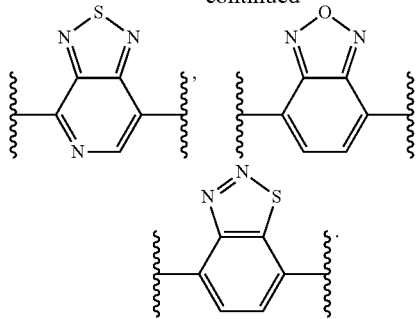 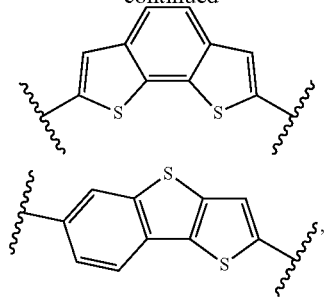
Examples of 5 to 12 membered heteroarylene are 5 to 9 membered heteroarylene and
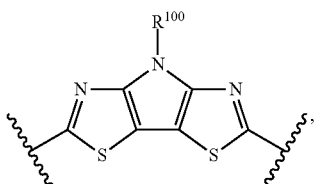
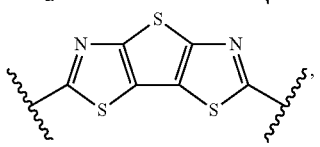
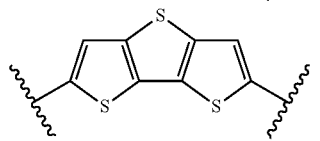
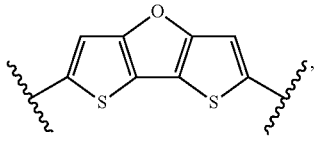
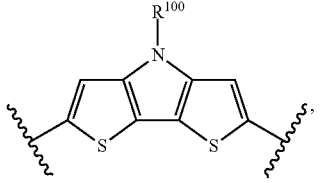
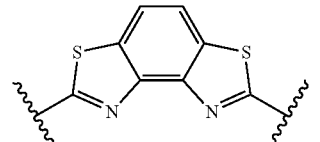
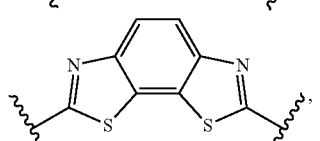
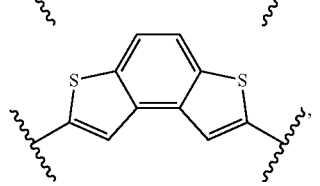
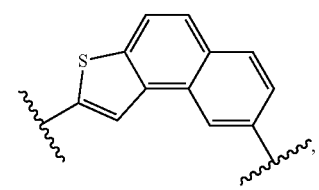
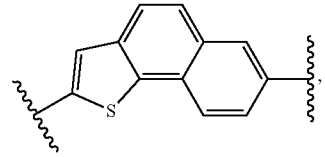
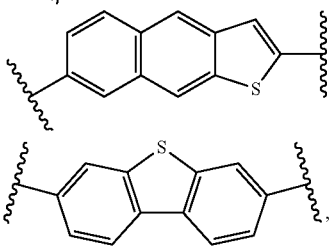
wherein $R^{100}$ is $C_{1-20}$-alkyl.
Examples of 5 to 15 membered heteroarylene are 5 to 12 membered heteroarylene and -continued

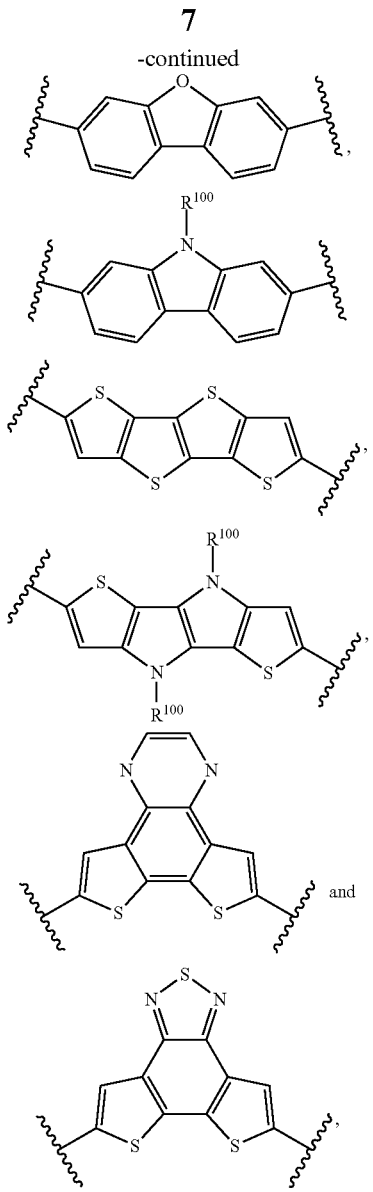

wherein R$^{100}$ is C$_{1-20}$-alkyl.
Examples of C$_{6-10}$-aryl are

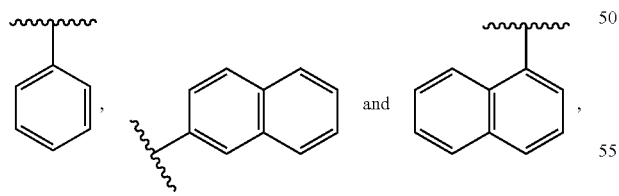

Examples of C$_{6-14}$-aryl are C$_{6-10}$-aryl and

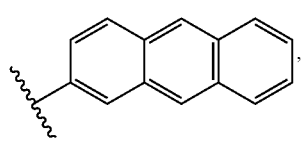

-continued

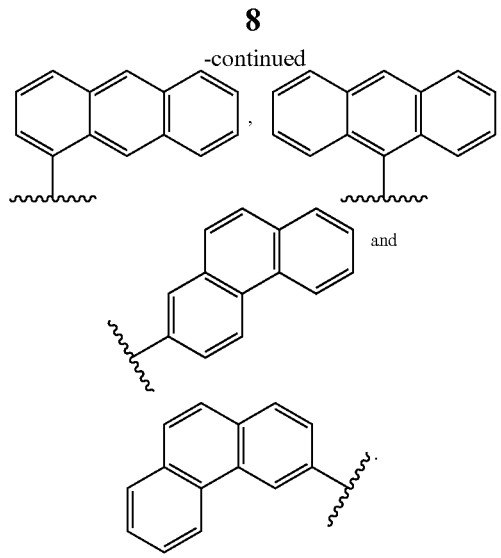

Examples of at least two adjacent Ar$^1$, respectively, at least two adjacent Ar$^2$ being additionally connected via an -(L)$_m$- linker are

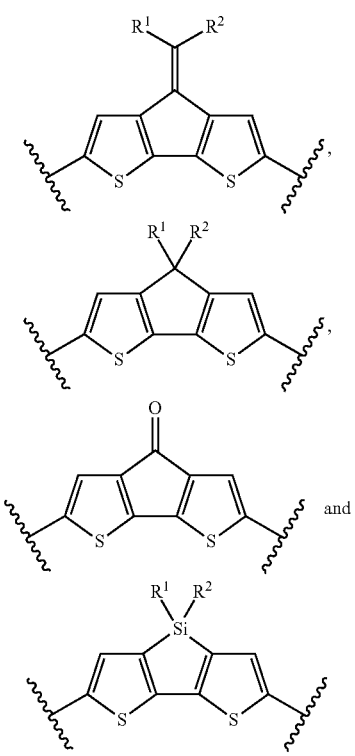

wherein R$^1$ and R$^2$ are individually from each other and at each occurrence H or C$_{1-20}$-alkyl.

Preferably, the polymers comprise at least 40% by weight of the units of formula (1) based on the weight of the polymer.

More preferably, the polymers comprise at least 60% by weight of the units of formula (1) based on the weight of the polymer.

Even more preferably, the polymers comprise at least 80% by weight of the units of formula (1) based on the weight of the polymer.

Most preferably, the polymers essentially consist of units of formula (1).

Preferably, $Ar^1$ and $Ar^2$ are independently from each other and at each occurrence $C_{6-14}$-arylene or a 5 to 12 membered heteroarylene,
  wherein $Ar^1$ and $Ar^2$ can be substituted with one to four substituents selected from the group consisting of $C_{1-30}$-alkyl, CN and $C_{6-14}$-aryl, and
  wherein at least two adjacent $Ar^1$, respectively, at least two adjacent $Ar^2$ can be additionally connected via an -$(L)_m$- linker,
    wherein L is at each occurrence selected from the group consisting of $CR^1R^2$, $C=CR^1R^2$, $C=O$ and $SiR^1R^2$, wherein $R^1$ and $R^2$ are individually from each other and at each occurrence H or $C_{1-20}$-alkyl, and m is 1 or 2.

More preferably, $Ar^1$ and $Ar^2$ are independently from each other and at each occurrence $C_{6-10}$-arylene or a 5 to 9 membered heteroarylene,
  wherein $Ar^1$ and $Ar^2$ can be substituted with one to four substituents selected from the group consisting of $C_{1-30}$-alkyl, CN and $C_{6-14}$-aryl, and
  wherein at least two adjacent $Ar^1$, respectively, at least two adjacent $Ar^2$ can be additionally connected via an -$(L)_m$- linker,
    wherein L is at each occurrence selected from the group consisting of $CR^1R^2$, $C=CR^1R^2$, $C=O$ and $SiR^1R^2$, wherein $R^1$ and $R^2$ are individually from each other and at each occurrence H or $C_{1-20}$-alkyl, and m is 1 or 2.

Even more preferably, $Ar^1$ and $Ar^2$ are independently from each other and at each occurrence a 5 to 9 membered heteroarylene,
  wherein $Ar^1$ and $Ar^2$ can be substituted with one to four substituents selected from the group consisting of $C_{1-30}$-alkyl, CN and $C_{1-14}$-aryl, and
  wherein at least two adjacent $Ar^1$, respectively, at least two adjacent $Ar^2$ can be additionally connected via an -$(L)_m$- linker,
    wherein L is at each occurrence selected from the group consisting of $CR^1R^2$, $C=CR^1R^2$, $C=O$ and $SiR^1R^2$, wherein $R^1$ and $R^2$ are individually from each other and at each occurrence H or $C_{1-20}$-alkyl, and m is 1 or 2.

Most preferably, $Ar^1$ and $Ar^2$ are independently from each other and at each occurrence a 5 membered heteroarylene,
  wherein $Ar^1$ and $Ar^2$ can be substituted with one to four substituents selected from the group consisting of $C_{1-30}$-alkyl, CN and $C_{6-14}$-aryl.

In particular preferred, $Ar^1$ and $Ar^2$ are both

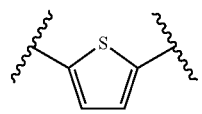 [SMILES: *c1ccc(*)s1]

which can be substituted with one or two $C_{1-30}$-alkyl.

Preferably,
o is an integer from 1 to 6, and
n is an integer from 1 to 6.

More preferably,
o is an integer from 1 to 4, and
n is an integer from 1 to 4.

Most preferably,
o is an integer from 1 to 3, and
n is an integer from 1 to 3.

In preferred polymers comprising at least one unit of formula (1)
  $Ar^1$ and $Ar^2$ are independently from each other and at each occurrence $C_{6-14}$-arylene or a 5 to 12 membered heteroarylene,
    wherein $Ar^1$ and $Ar^2$ can be substituted with one to four substituents selected from the group consisting of $C_{1-30}$-alkyl, CN and $C_{6-14}$-aryl, and
    wherein at least two adjacent $Ar^1$, respectively, at least two adjacent $Ar^2$ can be additionally connected via an -$(L)_m$- linker,
      wherein L is at each occurrence selected from the group consisting of $CR^1R^2$, $C=CR^1R^2$, $C=O$ and $SiR^1R^2$, wherein $R^1$ and $R^2$ are individually from each other and at each occurrence H or $C_{1-20}$-alkyl, and m is 1 or 2,
  o is an integer from 1 to 8, and
  n is an integer from 1 to 8.

In more preferred polymers comprising at least one unit of formula (1)
  $Ar^1$ and $Ar^2$ are independently from each other and at each occurrence $C_{6-10}$-arylene or a 5 to 9 membered heteroarylene,
    wherein $Ar^1$ and $Ar^2$ can be substituted with one to four substituents selected from the group consisting of $C_{1-30}$-alkyl, CN and $C_{6-14}$-aryl, and
    wherein at least two adjacent $Ar^1$, respectively, at least two adjacent $Ar^2$ can be additionally connected via an -$(L)_m$- linker,
      wherein L is at each occurrence selected from the group consisting of $CR^1R^2$, $C=CR^1R^2$, $C=O$ and $SiR^1R^2$, wherein $R^1$ and $R^2$ are individually from each other and at each occurrence H or $C_{1-20}$-alkyl, and m is 1 or 2,
  o is an integer from 1 to 6, and
  n is an integer from 1 to 6.

In even more preferred polymers comprising at least one unit of formula (1)
  $Ar^1$ and $Ar^2$ are independently from each other and at each occurrence a 5 to 9 membered heteroarylene,
    wherein $Ar^1$ and $Ar^2$ can be substituted with one to four substituents selected from the group consisting of $C_{1-30}$-alkyl, CN and $C_{6-14}$-aryl, and
    wherein at least two adjacent $Ar^1$, respectively, at least two adjacent $Ar^2$ can be additionally connected via an -$(L)_m$- linker,
      wherein L is at each occurrence selected from the group consisting of $CR^1R^2$, $C=CR^1R^2$, $C=O$ and $SiR^1R^2$, wherein $R^1$ and $R^2$ are individually from each other and at each occurrence H or $C_{1-20}$-alkyl, and m is 1 or 2,
  o is an integer from 1 to 6, and
  n is an integer from 1 to 6.

In most preferred polymers comprising at least one unit of formula (1)
  $Ar^1$ and $Ar^2$ are independently from each other and at each occurrence a 5 membered heteroarylene,
    wherein $Ar^1$ and $Ar^2$ can be substituted with one to four substituents selected from the group consisting of $C_{1-30}$-alkyl, CN and $C_{6-14}$-aryl,
  o is an integer from 1 to 4, and
  n is an integer from 1 to 4.

In particular preferred polymers comprising at least one unit of formula (1) Ar¹ and Ar² are both

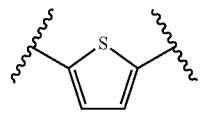

which can be substituted by $C_{1-30}$-alkyl, and
o is an integer from 1 to 3, and
n is an integer from 1 to 3.
An especially preferred polymer is

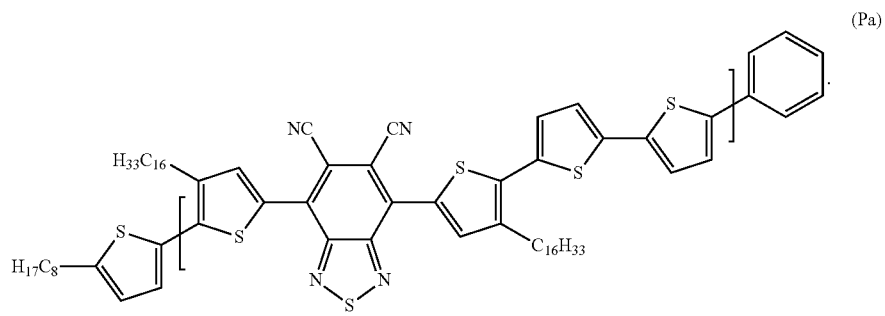

The compound of formula

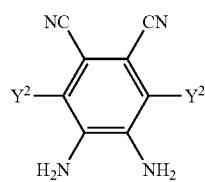

(5)

wherein
$Y^2$ is at each occurrence I, Br, Cl or O—S(O)$_2$CF$_3$,
can be prepared by treating a compound of formula

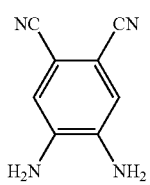

(6)

with an $Y^2$ donor agent, wherein $Y^2$ is as defined for the compound of formula (5).

The reaction conditions depend on the $Y^2$-donor. If the $Y^2$-donor, for example, is hydrobromic acid in combination with hydrogen peroxide, the reaction is usually performed by first adding hydrobromic acid to compound (6), followed by addition of hydrogen peroxide at temperatures in the range of −5 to 10° C., preferably at 0° C. The reaction can be performed in the presence of a suitable solvent such as methanol.

A preferred process for the preparation of the polymers comprising at least one unit of formula

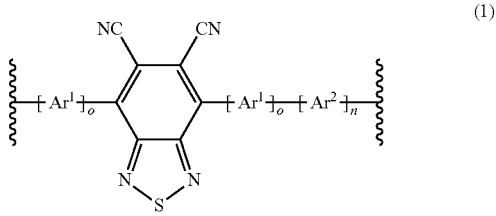

(1)

wherein
Ar¹ and Ar² are independently from each other and at each occurrence $C_{6-14}$-arylene or a 5 to 15 membered heteroarylene,
wherein Ar¹ and Ar² can be substituted with one to four substituents selected from the group consisting of $C_{1-30}$-alkyl, CN and $C_{6-14}$-aryl, and
wherein at least two adjacent Ar¹, respectively, at least two adjacent Ar² can be additionally connected via an -(L)$_m$- linker,
wherein L is at each occurrence selected from the group consisting of CR¹R², C=CR¹R², C=O and SiR¹R², wherein R¹ and R² are individually from each other and at each occurrence H or $C_{1-20}$-alkyl, and m is 1 or 2,
o is an integer from 1 to 8, and
n is an integer from 1 to 8,
which process comprises the steps of
(i) treating a compound of formula

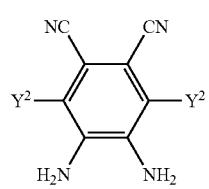

(5)

wherein
$Y^2$ is I, Br, Cl or O—S(O)$_2$CF$_3$,
with an S-donor agent, in order to obtain the compound of formula

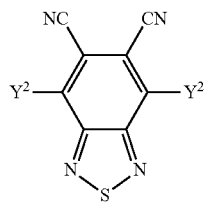  (4)

wherein $Y^2$ is as defined for the compound of formula (5),
(ii) treating the compound of formula (4) as obtained in step (i)
with a compound of formula

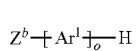  (9)

wherein
$Ar^1$ and o are as defined for the polymers comprising at least one unit of formula (1), and
$Z^b$ is selected from the group consisting of $B(OZ^1)(OZ^2)$, $SnZ^1Z^2Z^3$,

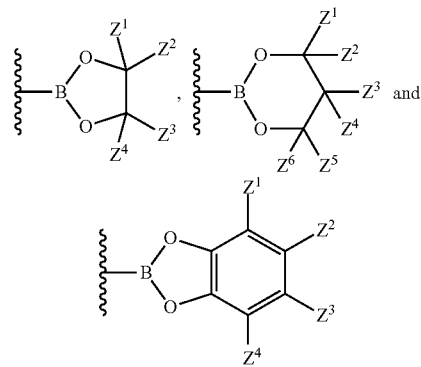

wherein $Z^1$, $Z^2$, $Z^3$, $Z^4$, $Z^5$ and $Z^6$ are independently from each other and at each occurrence H or $C_{1-6}$-alkyl,
in the presence of catalyst II,
in order to obtain a compound of formula

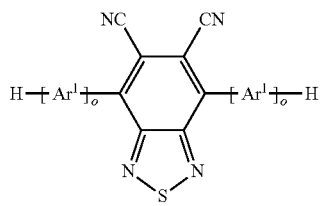  (3)

wherein
$Ar^1$ and o are as defined for the polymers comprising at least one unit of formula (1), and
(iii) treating a compound of formula (3) as obtained in step (ii) with a $Y^1$-donor agent, wherein
$Y^1$ is I, Br, Cl or $O-S(O)_2CF_3$, in order to obtain the compound of formula

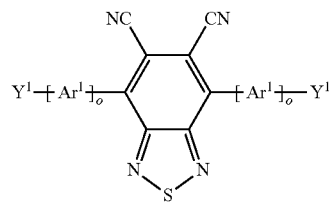  (2)

wherein
$Ar^1$ and o are as defined for the polymers comprising at least one unit of formula (1), and
$Y^1$ is at each occurrence I, Br, Cl or $O-S(O)_2CF_3$,
(iv) treating a compound of formula (2) as obtained in step (iii) with a compound of formula

  (8)

wherein
$Ar^1$ and n are as defined for the polymers comprising at least one unit of formula (1), and
$Z^a$ is at each occurrence selected from the group consisting of $B(OZ^1)(OZ^2)$, $SnZ^1Z^2Z^3$,

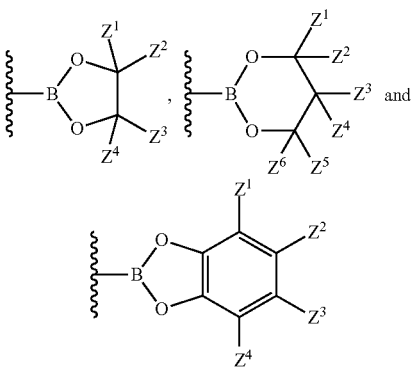

wherein $Z^1$, $Z^2$, $Z^3$, $Z^4$, $Z^5$ and $Z^6$ are independently from each other and at each occurrence H or $C_{1-6}$-alkyl,
in the presence of catalyst I,
in order to obtain polymers comprising at least one unit of formula (1).

The reaction conditions of step (iii) depend on the $Y^1$-donor. If the $Y^1$-donor, for example, is N-bromosuccinimide (NBS) the reaction is usually performed at ambient temperatures, such as at temperatures in the range of 15 to 30° C., preferably at room temperature. The reaction can be performed in the presence of a suitable solvent such as mixtures of chloroform and acetic acid.

When $Z^a$, respectively, $Z^b$ is selected from the group consisting of $B(OZ^1)(OZ^2)$,

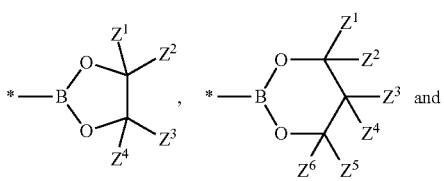

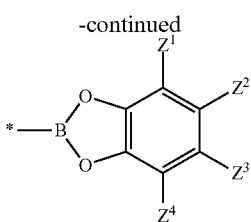

wherein $Z^1$, $Z^2$, $Z^3$, $Z^4$, $Z^5$ and $Z^6$ are independently from each other and at each occurrence H or $C_{1-6}$-alkyl, catalyst I, respectively, catalyst II is preferably a Pd catalyst such as $Pd(P(Ph)_3)_4$, $Pd(OAc)_2$ or $Pd_2(dba)_3$ in combination with a base such as $K_3PO_4$, $Na_2CO_3$, $K_2CO_3$, LiOH or NaOMe. Depending on the Pd catalyst, the reaction may also require the presence of a phosphine ligand such as $P(Ph)_3$, $P(o\text{-tolyl})_3$ and $P(\text{tert-Bu})_3$. The reaction is usually performed at elevated temperatures, such as at temperatures in the range of 40 to 250° C., preferably 60 to 200° C. The reaction can be performed in the presence of a suitable solvent such as tetrahydrofuran, toluene or chlorobenzene. The reaction is usually performed under inert gas.

When $Z^a$, respectively, $Z^b$ is $SnZ^1Z^2Z^3$, wherein $Z^1$, $Z^2$ and $Z^3$ are independently from each other and at each occurrence $C_{1-6}$-alkyl, catalyst I, respectively, catalyst II is preferably a Pd catalyst such as $Pd(P(Ph)_3)_4$ or $Pd_2(dba)_3$. Depending on the Pd catalyst, the reaction may also require the presence of a phosphine ligand such as $P(Ph)_3$, $P(o\text{-tolyl})_3$ and $P(\text{tert-Bu})_3$. The reaction is also usually performed at elevated temperatures, such as at temperatures in the range of 40 to 250° C., preferably 60 to 200° C. The reaction can be performed in the presence of a suitable solvent such as toluene or chlorobenzene. The reaction is usually performed under inert gas.

Also part of the present invention is a process for the preparation of a compound of

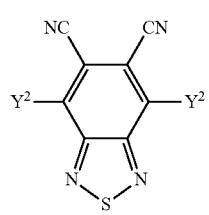

wherein $Y^2$ is I, Br, Cl or $O\text{—}S(O)_2CF_3$, which process comprises the step of treating a compound of formula

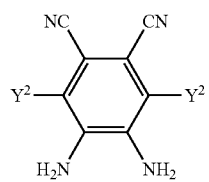

wherein
$Y^2$ is as defined for the compound of formula (4)
with an S-donor agent.

Also part of the present invention the compound of

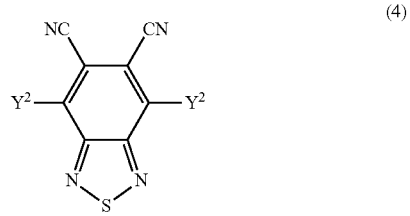

wherein $Y^2$ is I, Br, Cl or $O\text{—}S(O)_2CF_3$.

The polymers comprising at least one unit of formula (1) can be used as semiconducting material in electronic devices. The electronic device can be an organic photovoltaic device (OPVs), an organic field-effect transistor (OFETs), an organic light emitting diode (OLEDs) or an organic photodiode (OPDs).

The process of the present invention for the preparation of the polymers comprising at least one unit of formula (1) is advantageous as it starts from the intermediate compound of formula (4), which allows the easy incorporation of various $Ar^1$ and $Ar^2$. The process of the present invention is also advantageous as it is technically feasible as well as economic and ecologic and thus suitable for being used to manufacture the polymers comprising at least one unit of formula (1) on larger scales. The process described by Casey et al., for example, requires crone ether in order to replace the F-groups by CN-groups. However, crone ethers are toxic as well as expensive and thus the process described by Casey et al. is not suitable for being used to manufacture the polymers comprising at least one unit of formula (1) on larger scales.

FIG. 1 shows the transfer curves measured at various drain voltages $V_{DS}$ of a bottom-gate, bottom-contact field effect transistor comprising polymer Pa as semiconductor.

EXAMPLE 1

Preparation of Compound 4a

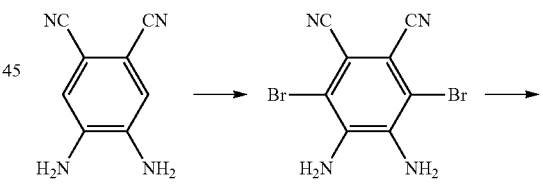

Preparation of Compound 5a

Compound 6 (1 g, 6.32 mmol) was dissolved in methanol (110 mL) under argon atmosphere, potassium bromide was added and the mixture was cooled down to 0° C. Hydrobromic acid (62 wt %, 2.01 eq, 12.68 mmol, 1.12 mL) was added dropwise, followed by dropwise addition of tert-butylhydroperoxide 70 wt % (4.01 eq., 25.37 mmol, 0.55 mL). The addition of hydrogen peroxide was repeated two to three times after stirring at room temperature for 24 hours each time. The reaction was continuously monitored by FD-MS and $^1$H-NMR spectroscopy. After completion of the reaction, the crude product was filtered off, washed with methanol and the solid residue was subjected to soxhlet-extraction with DCM for 5 days. After precipitation from DCM the compound 5a was obtained as a pale red solid. Yield: 1.176 g, 3.72 mmol, 59%. $^1$H-NMR: δ (300 MHz, DMSO-$d^6$)=6.42 (s, 4H). $^{13}$C-NMR: δ (300 MHz, DMSO-$d^6$)=105.94, 105.99, 116.33, 136.88. FD-MS: m/z=315.4 (calc. 315.9). HRMS (ESI): 316.8919 (MH$^+$); Calcd. for $C_8H_5N_4Br_2$: 316.9595.

Preparation of Compound 4a

Compound 5a (1.51 g, 5.18 mmol) was stirred in 60 mL freshly distilled thionyl chloride under argon atmosphere for 18 h at 55° C. The reaction mixture was poured into a mixture of half-concentrated solution of potassium carbonate and ice. The aqueous phase was extracted three times with ethyl acetate. The combined organic layers were dried with magnesium sulfate and the solvent was evaporated. The crude products were purified by column chromatography (dichloromethane:hexane, v:v=1:1) to yield 915.9 mg, (2.680 mmol, 52%) of compound 4a as an orange solid. $^{13}$C-NMR: δ (300 MHz, CD$_2$Cl$_2$)=114.88, 118.30, 123.50, 154.06. FD-MS: m/z=343.5 (calc. 343.8). HRMS (ESI): 366.8118 (MNa$^+$); Calcd. for $C_8N_4Br_2SNa$: 366.9751.

EXAMPLE 2

Preparation of Compound 3a

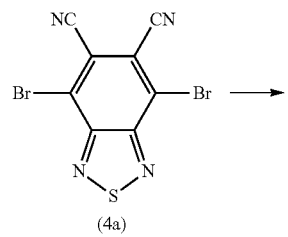

(4a)

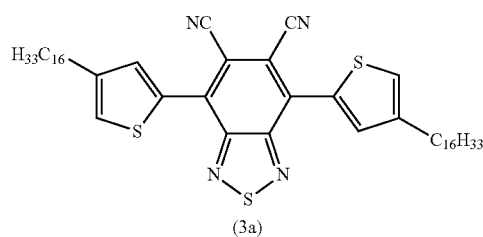

(3a)

Compound 4a (400 mg, 1.163 mmol) and tributyl(4-hexadecylthiophen-2-yl)stannane (62.5% solution 2.053 g, 2.442 mmol) were dissolved in 15 mL o-dichlorobenzene and the solution was degassed through bubbling with argon for 15 minutes. Tetrakis(triphenylphosphine)palladium(0) (268.7 mg, 0.233 mmol) was added and the solution was stirred at 130° C. for 48 hours. After cooling down to room temperature, the mixture was poured on water, the organic phase was separated and the aqueous phase was extracted two times with dichloromethane. The combined organic phases were dried with sodium sulfate, filtered and the dichloromethane was evaporated. The crude product was purified by column chromatography (hexane:dichloromethane, v:v=2:1) to yield 572.6 mg (0.573 mmol, 49%) of compound 3a as an orange solid.

$^1$H-NMR: δ (500 MHz, C$_2$D$_2$Cl$_4$)=0.81 (t, 6H), 1.07-1.47 (m, 52H), 1.65 (p, 6H), 2.66 (t, 4H) 7.42 (d, 2H), 7.93 (d, 2H). $^{13}$C-NMR: δ (500 MHz, C$_2$D$_2$Cl$_4$)=14.13, 22.77, 29.44, 29.46, 29.46, 29.73, 29.82, 30.57, 32.06, 110.93, 116.47, 127.52, 133.12, 133.43 134.11, 144.62, 153.66. FD-MS: m/z=798.4 (calc. 798.5). HRMS (ESI): 821.4656 (MNa$^+$); Calcd. for $C_{48}H_{70}N_4S_3Na$: 821.4660.

EXAMPLE 3

Preparation of Compound 2a

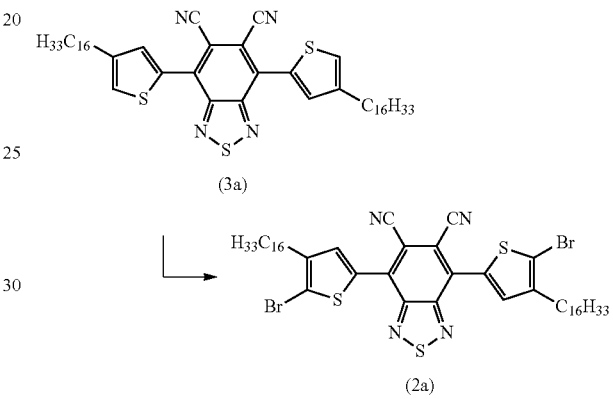

Compound 3a (320 mg, 0.4 mmol) and NBS (178.1 mg, 1,001 mmol) were dissolved in 150 mL chloroform/acetic acid 4:1 and the solution was degassed through bubbling with argon for 15 minutes. The mixture was stirred for 7 days at room temperature, while being monitored by thin-layer chromatography. Additional 0.5 (35.62 mg, 0.2 mmol), 1 (71.23 mg, 0.4 mmol) and 2 (142.47 mg, 0.8 mmol) equivalents of NBS had been added after 1, 2 and 5 days respectively. After completion of the reaction, the mixture was poured on water, the aqueous phase was extracted two times with dichloromethane. The combined organic phases were dried with sodium sulfate, filtered and the solvent was evaporated. The crude product was purified by column chromatography (hexane:dichloromethane, v:v=2:1) to yield 355.1 mg (0.371 mmol, 93%) of compound 2a as an red solid. $^1$H-NMR: δ (300 MHz, CD$_2$Cl$_2$)=0.87 (t, 6H), 1.37 (m, 52H), 1.68 (p, 4H), 2.70 (t, 4H), 7.97 (s, 2H). $^{13}$C-NMR: δ (300 MHz, CD$_2$Cl$_2$)=14.45, 23.27, 29.74, 29.94, 29.97, 30.03, 30.15, 30.23, 30.27, 32.50, 110.71, 116.89, 118.46, 132.38, 133.36, 133.80, 143.97, 153.46. FD-MS: m/z=956.3 (calc. 956.3).

EXAMPLE 4

Preparation of Polymer Pa

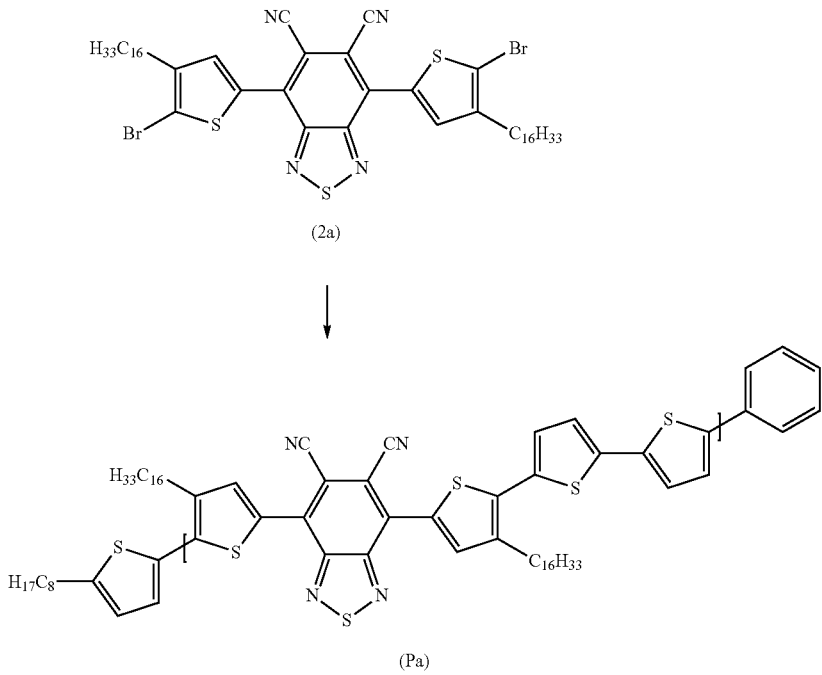

Compound 2a (200 mg, 0.209 mmol), 5,5'-bis(trimethylstannyl)-2,2'-bithiophene (102.8 mg, 0.209 mmol) and tri(o-tolyl)phosphine (51.3 mg, 0.168 mmol) were dissolved in 25 mL of o-dichlorobenzene and the solution was degassed through bubbling with argon for 30 minutes. Dipalladium-tris(dibenzylideneacetone) (14.5 mg, 0.014 mmol) was added and the solution was stirred at 130° C. for 48 hours. Trimethyl(5-octylthiophen-2-yl)stannane was added and stirring of the solution was continued for 8 hours at 130° C. After adding bromobenzene and stirring for further 12 hours, the mixture was cooled to room temperature. The polymer was precipitated in 250 mL from methanol, filtered, solved in hot chloroform and stirred with BASOLITE® 100 FOR 30 minutes to remove metal salts. After filtration of BASOLITE and precipitation from methanol once again, the crude material was purified by Sohxlet extraction using methanol, ethyl acetate and petrol ether. Polymer Pa was collected and dried under vacuum (192.48 mg, 94%). $^1$H-NMR: δ (500 MHz, $C_2D_2Cl_4$)=0.79-0.99 (m), 1.10-1.64 (m), 5.55-6.50 (m), 7.23-8.01 (m). Gel-permeation chromatography (GPC) analysis against polystyrene standards in 1,2,4-trichlorobenzene (TCB) using refractive index detector (RI-detector) exhibited a number-averaged molecular weight ($M_n$) of $8.8 \cdot 10^3$ g/mol and a weight-averaged molecular weight (Mw) of $13.9 \cdot 10^3$ g/mol, giving a polydispersity index (PDI) of 1.59. Thermogravimetric analysis (TGA) was performed on the polymer Pa. Pa shows an initial weight loss at 430° C. indicating high thermal stability of the polymer.

EXAMPLE 5

Preparation of Compound 3b

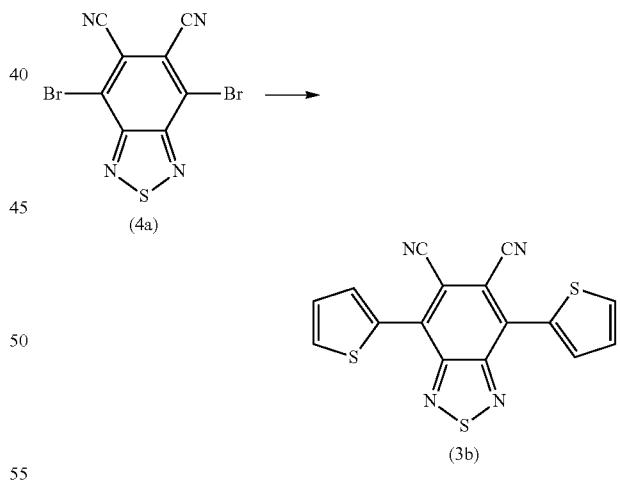

Compound 4a (300 mg, 0.872 mmol) and 0.55 mL tributyl(thiophen-2-yl)stannane (650.9 mg, 1.744 mmol) were dissolved in 15 mL o-dichlorobenzene and the solution was degassed through bubbling with argon for 15 minutes. Tetrakis(triphenylphosphine)palladium(0) (201.6 mg, 0.174 mmol) was added and the solution was stirred at 130° C. for 48 hours. After cooling down to room temperature, the mixture was poured on water, the organic phase was separated and the aqueous phase was extracted two times with dichloromethane. The combined organic phases were dried with sodium sulfate, filtered and the dichloromethane was evaporated. The crude product was purified by column chromatography (hexane:dichloromethane, v:v=2:1) to yield 136.2 mg (0.389 mmol, 45%) of compound 3b as an orange solid. $^1$H-NMR: δ (300 MHz, CD$_2$Cl$_2$)=7.35 (dd, 2H), 7.83 (dd, 2H), 8.17 (dd, 2H). $^{13}$C-NMR: δ (300 MHz, CD$_2$Cl$_2$)=111.51, 116.92, 128.32, 132.74, 133.02, 133.75, 133.81, 153.94. FD-MS: m/z=349.5 (calc. 350.0). HRMS (ESI): 372.9664 (MNa$^+$); Calcd. for C$_{16}$H$_6$N$_4$S$_3$Na: 372.9652.

EXAMPLE 6

Preparation of Compound 3c

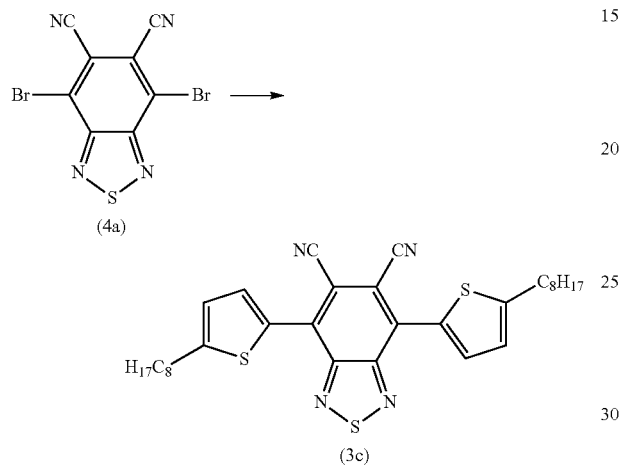

Compound 4a (200 mg, 0.581 mmol) and 0.51 mL tributyl(5-octylthiophen-2-yl)stannane (593.7 mg, 1.221 mmol) were dissolved in 10 mL o-dichlorobenzene and the solution was degassed through bubbling with argon for 15 minutes. Tetrakis(triphenylphosphine)palladium(0) (134.4 mg, 0.116 mmol) was added and the solution was stirred at 130° C. for 48 hours. After cooling down to room temperature, the mixture was poured on water, the organic phase was separated and the aqueous phase was extracted two times with dichloromethane. The combined organic phases were dried with sodium sulfate, filtered and the dichloromethane was evaporated. The crude product was purified by column chromatography (hexane:dichloromethane, v:v=2:1) to yield 129.7 mg (0.226 mmol, 39%) of compound 3c as an red solid.

EXAMPLE 7

Preparation of a Bottom-Gate, Bottom-Contact Field Effect Transistor Comprising Polymer Pa as Semiconductor The source and drain electrodes with 60 nm in thickness were deposited by Au evaporation. The channel lengths and widths are 20 and 1400 μm, respectively. A 300 nm thick SiO$_2$ dielectric covering the highly doped Si acting as the gate electrode was functionalized with hexamethyldisilazane (HMDS) to minimize interfacial trapping sites. Polymer Pa thin films were deposited by drop-casting 2 mg mL$^{-1}$ of a solution of polymer Pa in 1,2 dichlorobenzene on the hot field effect transistor precursor (100° C.) in nitrogen atmosphere, followed by annealing at 120° C. for 30 min. The channel lengths and widths are 20 and 1400 μm, respectively.

Electrical measurements were performed using Keithley 4200 SCS in a glove-box under nitrogen atmosphere.

The transfer curves measured at various drain voltages V$_{DS}$ are depicted in FIG. 1.

The field effect mobility was calculated from the transfer curves in the saturation regime using the equation:

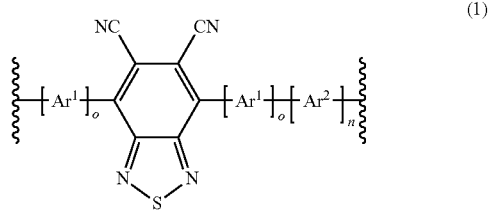

where: L denotes the channel length; W denotes the channel width; C$_i$ denotes the capacitance per unit area; I$_{DS}$ denotes the drain source current; V$_{GS}$ denotes the gate voltage; and α denotes the slope obtained by linear fitting of plots of the square-root of the drain current versus the gate voltage (V$_{GS}$).

The ambipolar behaviour of Pa is clearly evident from the output characteristic in both p- and n-type operation modes for negative and positive gate voltages with mobility of 6×10$^{-4}$ cm$^2$ V$^{-1}$ s$^{-1}$ for holes and 1×10$^{-4}$ cm$^2$ V$^{-1}$ s$^{-1}$ for electrons.

The invention claimed is:

1. A process for the preparation of a polymer comprising at least one unit of formula (1)

[structure of formula (1)]

wherein
Ar$^1$ and Ar$^2$ are independently from each other and at each occurrence C$_{6-14}$-arylene or a 5 to 15 membered heteroarylene,
wherein Ar$^1$ and Ar$^2$ can be substituted with one to four substituents selected from the group consisting of C$_{1-30}$-alkyl, CN and C$_{6-14}$-aryl, and
wherein at least two adjacent Ar$^1$, respectively, at least two adjacent Ar$^2$ can be connected via an -(L)$_m$- linker,
wherein L is at each occurrence selected from the group consisting of CR$^1$R$^2$, C=CR$^1$R$^2$, C=O and SiR$^1$R$^2$, wherein R$^1$ and R$^2$ are individually from each other and at each occurrence H or C$_{1-20}$-alkyl, and m is 1 or 2,
o is an integer from 1 to 8, and
n is an integer from 1 to 8,
said process comprising
(i) treating a compound of formula

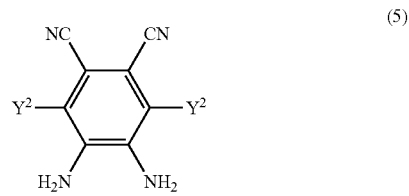

(5)

wherein
$Y^2$ is I, Br, Cl or O—S(O)$_2$CF$_3$,
with an S-donor agent, in order to obtain the compound of formula

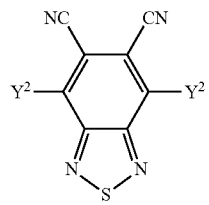

(4)

wherein $Y^2$ is as defined for the compound of formula (5).

2. The process of claim 1, wherein in the polymer comprising at least one unit of formula (1)
   $Ar^1$ and $Ar^2$ are independently from each other and at each occurrence C$_{6-10}$-arylene or a 5 to 9 membered heteroarylene,
   wherein $Ar^1$ and $Ar^2$ can be substituted with one to four substituents selected from the group consisting of C$_{1-30}$-alkyl, CN and C$_{6-14}$-aryl, and
   wherein at least two adjacent $Ar^1$, respectively, at least two adjacent $Ar^2$ can be connected via an -(L)$_m$- linker,
   wherein L is at each occurrence selected from the group consisting of CR$^1$R$^2$, C=CR$^1$R$^2$, C=O and SiR$^1$R$^2$,
   wherein R$^1$ and R$^2$ are individually from each other and at each occurrence H or C$_{1-20}$-alkyl, and m is 1 or 2.

3. The process of claim 2, wherein in the polymer comprising at least one unit of formula (1)
   $Ar^1$ and $Ar^2$ are independently from each other and at each occurrence a 5 to 9 membered heteroarylene,
   wherein $Ar^1$ and $Ar^2$ can be substituted with one to four substituents selected from the group consisting of C$_{1-30}$-alkyl, CN and C$_{6-14}$-aryl, and
   wherein at least two adjacent $Ar^1$, respectively, at least two adjacent $Ar^2$ can be connected via an -(L)$_m$- linker,
   wherein L is at each occurrence selected from the group consisting of CR$^1$R$^2$, C=CR$^1$R$^2$, C=O and SiR$^1$R$^2$,
   wherein R$^1$ and R$^2$ are individually from each other and at each occurrence H or C$_{1-20}$-alkyl, and m is 1 or 2.

4. The process of claim 3, wherein in the polymer comprising at least one unit of formula (1)
   $Ar^1$ and $Ar^2$ are independently from each other and at each occurrence a 5 membered heteroarylene,
   wherein $Ar^1$ and $Ar^2$ can be substituted with one to four substituents selected from the group consisting of C$_{1-30}$-alkyl, CN and C$_{6-14}$-aryl.

5. The process of claim 4, wherein in the polymer comprising at least one unit of formula (1)
   o is an integer from 1 to 6, and
   n is an integer from 1 to 6.

6. The process of claim 5, wherein in the polymer comprising at least one unit of formula (1)
   o is an integer from 1 to 4, and
   n is an integer from 1 to 4.

7. The process of claim 1, further comprising
   (ii) treating the compound of formula (4) as obtained in step (i)
   with a compound of formula

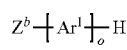

(9)

wherein
$Ar^1$ and o are as defined for the polymer comprising at least one unit of formula (1), and
$Z^b$ is selected from the group consisting of B(OZ$^1$)(OZ$^2$), SnZ$^1$Z$^2$Z$^3$,

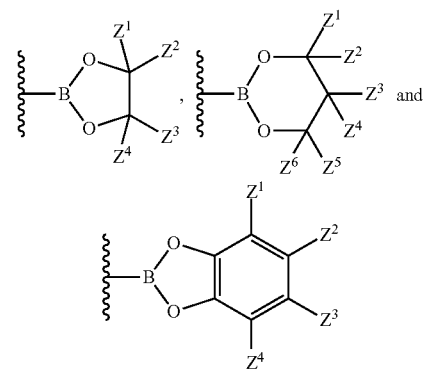

wherein $Z^1$, $Z^2$, $Z^3$, $Z^4$, $Z^5$ and $Z^6$ are independently from each other and at each occurrence H or C$_{1-6}$-alkyl,
in the presence of catalyst II,
in order to obtain a compound of formula

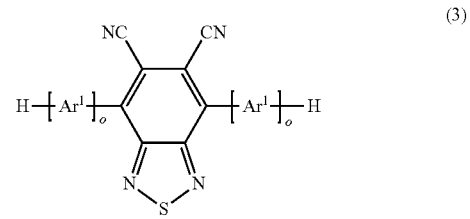

(3)

wherein
$Ar^1$ and o are as defined for the polymer comprising at least one unit of formula (1), and
(iii) treating a compound of formula (3) as obtained in step (ii) with a $Y^1$-donor agent, wherein $Y^1$ is I, Br, Cl or O—S(O)$_2$CF$_3$, in order to obtain the compound of formula

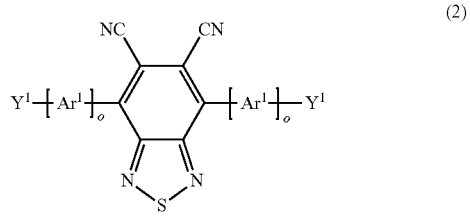

(2)

wherein
$Ar^1$ and o are as defined for the polymer comprising at least one unit of formula (1), and
$Y^1$ is at each occurrence I, Br, Cl or O—S(O)$_2$CF$_3$,
(iv) treating a compound of formula (2) as obtained in step (iii) with a compound of formula

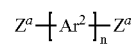

(8)

wherein

Ar² and n are as defined for the polymer comprising at least one unit of formula (1), and $Z^a$ is at each occurrence selected from the group consisting of $B(OZ^1)(OZ^2)$, $SnZ^1Z^2Z^3$,

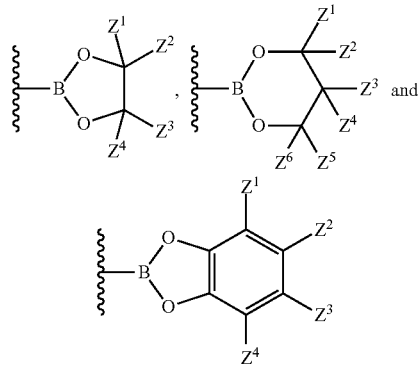

wherein $Z^1$, $Z^2$, $Z^3$, $Z^4$, $Z^5$ and $Z^6$ are independently from each other and at each occurrence H or $C_{1-6}$-alkyl, in the presence of catalyst I, in order to obtain the polymer comprising at least one unit of formula (1).

8. A process for the preparation of a compound of

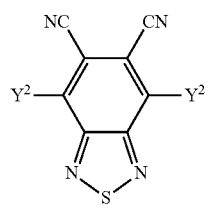

(4)

wherein $Y^2$ is I, Br, Cl or $O\!-\!S(O)_2CF_3$, said process comprising treating a compound of formula

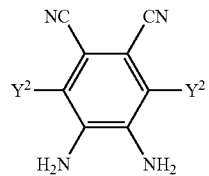

(5)

wherein $Y^2$ is as defined for the compound of formula (4)

with an S-donor agent.

9. The compound of

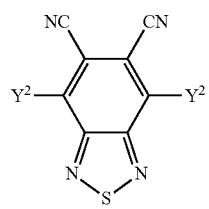

(4)

wherein $Y^2$ is I, Br, Cl or $O\!-\!S(O)_2CF_3$.

* * * * *